United States Patent
Papini et al.

(10) Patent No.: US 10,682,088 B2
(45) Date of Patent: Jun. 16, 2020

(54) METHOD AND APPARATUS FOR MONITORING THE INGESTION OF FOOD AND/OR DRINK BY A SUBJECT

(71) Applicant: KONINKLIJKE PHILIPS N.V., Eindhoven (NL)

(72) Inventors: Gabriele Papini, Eindhoven (NL); Francesco Sartor, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 176 days.

(21) Appl. No.: 15/775,125

(22) PCT Filed: Dec. 7, 2016

(86) PCT No.: PCT/EP2016/079967
§ 371 (c)(1),
(2) Date: May 10, 2018

(87) PCT Pub. No.: WO2017/108396
PCT Pub. Date: Jun. 29, 2017

(65) Prior Publication Data
US 2018/0325444 A1 Nov. 15, 2018

(30) Foreign Application Priority Data

Dec. 21, 2015 (EP) .................................. 15201587

(51) Int. Cl.
*A61B 5/00* (2006.01)
*A61B 5/0205* (2006.01)
(Continued)

(52) U.S. Cl.
CPC .......... *A61B 5/4238* (2013.01); *A61B 5/0205* (2013.01); *A61B 5/061* (2013.01);
(Continued)

(58) Field of Classification Search
CPC .............. A61B 5/0205; A61B 5/02055; A61B 5/04005; A61B 5/05; A61B 5/0515;
(Continued)

(56) References Cited

U.S. PATENT DOCUMENTS

| 4,079,730 A | * | 3/1978 | Wikswo, Jr. | ......... A61B 5/0265 600/504 |
| 5,794,622 A | * | 8/1998 | Chopp | ................. A61B 5/0265 600/431 |

(Continued)

FOREIGN PATENT DOCUMENTS

| WO | 2014159749 A1 | 10/2014 |
| WO | 2014163784 A1 | 10/2014 |

*Primary Examiner* — Eugene T Wu (57) ABSTRACT

There is provided an apparatus for monitoring the ingestion of food and/or drink by a subject, the apparatus comprising a control unit that comprises a first obtaining module configured to obtain measurements of one or more physiological characteristics of the subject; a second obtaining module configured to obtain measurements of eddy currents generated in the body of the subject by an externally-applied magnetic field; a setting module configured to set a respective cut-off frequency for one or more filtering stages based on a respective frequency for each of said one or more physiological characteristics; a filtering module configured to filter the measurements of eddy currents using the one or more filtering stages to remove signal components due to the one or more physiological characteristics; and a processing module configured to process the filtered measurements to determine whether food and/or drink is present in the stomach of the subject.

10 Claims, 5 Drawing Sheets

(51) Int. Cl.
*A61B 5/11* (2006.01)
*A61F 5/00* (2006.01)
*A61B 5/06* (2006.01)
*G16H 20/60* (2018.01)

(52) U.S. Cl.
CPC .......... *A61B 5/1118* (2013.01); *A61B 5/6823* (2013.01); *A61F 5/0009* (2013.01); *G16H 20/60* (2018.01); *A61B 5/062* (2013.01); *A61B 5/6802* (2013.01); *A61B 5/6805* (2013.01)

(58) Field of Classification Search
CPC ..... A61B 5/0522; A61B 5/053; A61B 5/0537; A61B 5/055; A61B 5/42; A61B 5/4238; A61B 5/4866; A61B 5/4869; A61B 5/7203; A61B 5/7207; A61B 5/721; A61B 5/7225; A61B 5/7283
See application file for complete search history.

(56) References Cited

U.S. PATENT DOCUMENTS

| | | | |
|---|---|---|---|
| 6,208,884 B1* | 3/2001 | Kumar | A61B 5/04005 |
| | | | 324/207.21 |
| 2006/0064037 A1 | 3/2006 | Shalon | |
| 2008/0097188 A1* | 4/2008 | Pool | A61B 5/05 |
| | | | 600/409 |
| 2008/0306373 A1 | 12/2008 | Kandori | |

* cited by examiner

METHOD AND APPARATUS FOR MONITORING THE INGESTION OF FOOD AND/OR DRINK BY A SUBJECT

This application is the U.S. National Phase application under 35 U.S.C. § 371 of International Application No. PCT/EP2016/079967, filed on Dec. 7, 2016, which claims the benefit of International Application No. 15201587.1 filed on Dec. 21, 2015. These applications are hereby incorporated by reference herein.

TECHNICAL FIELD

The invention relates to a method and apparatus for monitoring a subject, and in particular for monitoring the ingestion of food and/or drink by a subject.

BACKGROUND TO THE INVENTION

Over-eating is the main cause of obesity. In some cases, people are not always consciously aware that they are eating more than their body requires on a daily basis. Often, when over-eating occurs the person does not realise it until there has been a substantial increase in their body weight, and it can be too late to make a small change to their eating habits and improve the situation.

Typically, the monitoring of food intake in terms of events (i.e. when) and quantity is done with self-report diaries, but the effectiveness and quality of this data is down to the discipline of the person and the time they have available to fill them in.

There are several types of devices that can monitor food intake, but these are invasive and/or costly, and include devices such as manometry, scintigraphy, ultrasonography, electrogastrography (EGG), stable isotope breath testing. In addition, the use of these types of devices tends to be confined to the professional settings for the diagnosis of specific eating disorders.

There is therefore a need for an improved method and apparatus that provides a non-invasive and generally unobtrusive solution for monitoring the ingestion of food and/or drink by a subject.

SUMMARY OF THE INVENTION

According to a first aspect, there is provided an apparatus for monitoring the ingestion of food and/or drink by a subject, the apparatus having a control unit that comprises a first obtaining module for obtaining measurements of one or more physiological characteristics of the subject; a second obtaining module for obtaining measurements of eddy currents generated in the body of the subject by an externally-applied magnetic field; a setting module for setting a respective cut-off frequency for one or more filtering stages based on a respective frequency for each of said one or more physiological characteristics; a filtering module for filtering the measurements of eddy currents using the one or more filtering stages to remove signal components due to the one or more physiological characteristics; and a processing module for processing the filtered measurements to determine whether food and/or drink is present in the stomach of the subject.

In some embodiments, the one or more physiological characteristics comprises one or more of heart rate and breathing rate.

In some embodiments, the one or more filtering stages comprises one or more low-pass filtering stages.

In some embodiments, the processing module is configured to process the filtered measurements to determine whether food and/or drink is present in the stomach of the subject by comparing the amplitude of the filtered measurements at a time instant to a threshold.

In some embodiments, the processing module is further configured to process the filtered measurements to determine whether food and/or drink is present in the stomach of the subject by determining that food and/or drink is present in the stomach if the amplitude at the time instant is above the threshold. In alternative embodiments, the processing module is further configured to process the filtered measurements to determine whether food and/or drink is present in the stomach of the subject by processing the filtered measurements to identify a signal relating to peristalsis in the subject; and determining that food and/or drink is present in the stomach of the subject if the amplitude at the time instant is above the threshold and the signal relating to peristalsis indicates that peristalsis is occurring in the subject.

In alternative embodiments, the processing module is configured to process the filtered measurements to determine whether food and/or drink is present in the stomach of the subject by determining an amount by which the amplitude of the filtered measurements has changed over a predetermined time window; and comparing the amount by which the amplitude of the filtered measurements has changed over the predetermined time window to a threshold.

In some embodiments, the processing module is further configured to process the filtered measurements to determine whether food and/or drink is present in the stomach of the subject by determining that food and/or drink is present in the stomach if the amount is above the threshold. In alternative embodiments, the processing module is further configured to process the filtered measurements to determine whether food and/or drink is present in the stomach of the subject by processing the filtered measurements to identify a signal relating to peristalsis in the subject; and determining that food and/or drink is present in the stomach of the subject if the amount is above the threshold and the signal relating to peristalsis indicates that peristalsis is occurring in the subject.

In some embodiments, the apparatus further comprises an excitation coil for generating an eddy current in the subject; and a measurement coil for measuring the eddy current in the subject.

In some embodiments, the apparatus further comprises one or more physiological characteristic sensors for obtaining the measurements of the one or more physiological characteristics of the subject.

According to a second aspect, there is provided an apparatus for monitoring the ingestion of food and/or drink by a subject, the apparatus comprising a control unit that is configured to: obtain measurements of one or more physiological characteristics of the subject; obtain measurements of eddy currents generated in the body of the subject by an externally-applied magnetic field; set a respective cut-off frequency for one or more filtering stages based on a respective frequency for each of said one or more physiological characteristics; filter the measurements of eddy currents using the one or more filtering stages to remove signal components due to the one or more physiological characteristics; and process the filtered measurements to determine whether food and/or drink is present in the stomach of the subject.

According to a third aspect, there is provided a method for monitoring the ingestion of food and/or drink by a subject, the method comprising obtaining measurements of one or more physiological characteristics of the subject; obtaining measurements of eddy currents generated in the body of the subject by an externally-applied magnetic field; setting a respective cut-off frequency for one or more filtering stages based on a respective frequency for each of said one or more physiological characteristics; filtering the measurements of eddy currents using the one or more filtering stages to remove signal components due to the one or more physiological characteristics; and processing the filtered measurements to determine whether food and/or drink is present in the stomach of the subject. In some embodiments, the one or more physiological characteristics comprises one or more of heart rate and breathing rate.

In some embodiments, the one or more filtering stages comprises one or more low-pass filtering stages.

In some embodiments, the step of processing the filtered measurements to determine whether food and/or drink is present in the stomach of the subject further comprises comparing the amplitude of the filtered measurements at a time instant to a threshold.

In some embodiments, the step of processing the filtered measurements to determine whether food and/or drink is present in the stomach of the subject comprises determining that food and/or drink is present in the stomach if the amplitude at the time instant is above the threshold. In alternative embodiments, the step of processing further comprises processing the filtered measurements to identify a signal relating to peristalsis in the subject; and determining that food and/or drink is present in the stomach of the subject if the amplitude at the time instant is above the threshold and the signal relating to peristalsis indicates that peristalsis is occurring in the subject.

In alternative embodiments, the step of processing comprises determining an amount by which the amplitude of the filtered measurements has changed over a predetermined time window; and comparing the amount by which the amplitude of the filtered measurements has changed over the predetermined time window to a threshold.

In some embodiments, the step of processing comprises determining that food and/or drink is present in the stomach if the amount is above the threshold. In alternative embodiments, the step of processing comprises processing the filtered measurements to identify a signal relating to peristalsis in the subject; and determining that food and/or drink is present in the stomach of the subject if the amount is above the threshold and the signal relating to peristalsis indicates that peristalsis is occurring in the subject.

According to a fourth aspect, there is provided a computer program product comprising a computer readable medium having computer readable code embodied therein, the computer readable code being configured such that, on execution by a suitable computer or processor, the computer or processor performs any of the method embodiments above.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

After food is chewed by a subject, it passes through the esophagus and enters the stomach. In the stomach the food is mixed with hydrochloric acid and digestive enzymes (such as trypsin) and exposed to a mechanical action to reduce the size of the food chunks (to around 1 mm) to facilitate its absorption in the intestine. Food from the stomach is passed to the intestine via the pylorus valve, but this happens gradually over time. Only a small amount of chyme (the partly digested food that leaves the stomach) passes through this valve each time and at a low frequency. The presence of the food and chyme in the stomach changes the electrical and magnetic properties of this part of the body. In particular the presence of food in the stomach changes the strength of an eddy current generated inside the body by a magnetic field from that generated when the stomach is empty.

Thus, the invention monitors the ingestion of food and/or drink by the subject by sensing changes in the magnetic inductance of part of the subject's body (i.e. the part containing the stomach). Advantageously, the excitation magnetic field is applied by a coil or other component that is located outside the body of the subject, and the eddy current is measured using another coil or other component that is located outside the body, so the invention is non-invasive.

However, in some cases (for example depending on the type and/or volume of food and/or drink that has been consumed), the change in magnetic inductance caused by the presence of food and/or drink can be relatively small, and thus difficult to detect by applying a magnetic field and measuring the eddy current using a measuring component that is external to the body.

As the eddy current generated by the magnetic field is also generated in the tissue around the stomach (e.g. muscles, blood vessels, etc.), the eddy current is affected by changes in the composition of that tissue as well as changes in the contents of the stomach. For example, changes in blood volume in the measurement region (the region of the body in which the eddy current is generated and measured in) due to the beating of the heart can affect the eddy current, as can changes in the volume of the chest due to the subject's breathing. Likewise, the movement of the stomach in expelling chyme into the intestine (known as peristalsis) can affect the eddy current.

Generally, measurements of an eddy current will include a sinusoidal signal due to the beating of the heart (usually at a frequency higher than, for example, 0.6 Hz), a sinusoidal signal due to respiration (usually at a frequency higher than, for example, 0.2 Hz), a sinusoidal signal due to the peristaltic movement of the stomach (usually at a frequency of around, for example, 0.05-0.06 Hz) if food and/or drink is present in the stomach, a constant (DC) component due to the content/composition of the body that does not vary (e.g. a component due to organs and fluid), and a component that increases and decreases with the content of the stomach. The ingestion of food and/or drink into the stomach increases the latter component, and the passage of chyme from the stomach to the intestine decreases the latter component. It should be noted that the component due to the content of the stomach is not a periodic component (unlike the heart beat, respiration and peristaltic components above), but can change in a generally linear or step-wise manner.

Therefore, to increase the sensitivity of the food and/or drink detection (i.e. the detection of the component that increases and decreases with the content of the stomach), the invention measures a physiological characteristic of the subject that affects the eddy current measurements (for example heart rate and/or respiration rate) and filters out eddy current signal components that may be related to that physiological characteristic.

Figure 1:
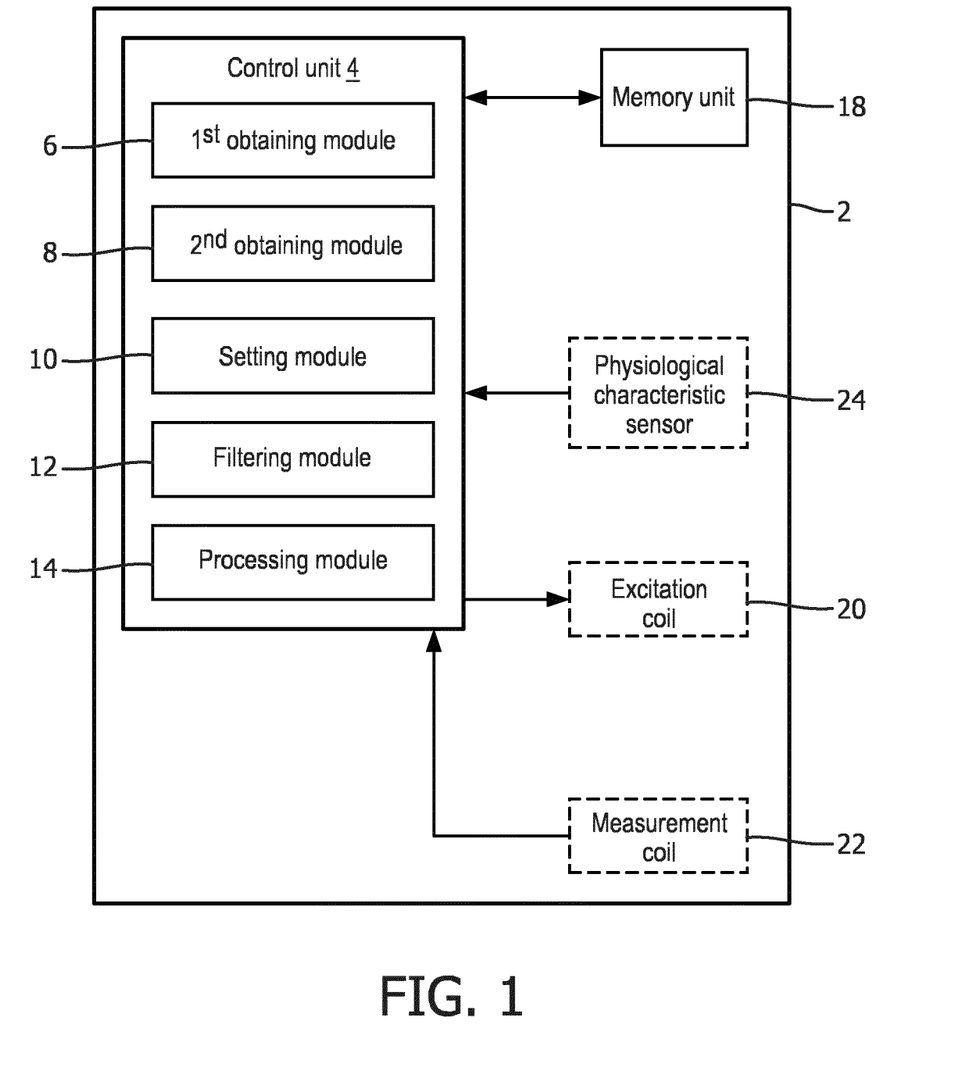
FIG. 1 is a block diagram of an apparatus according to an embodiment of the invention.

FIG. 1 shows a block diagram of an apparatus 2 according to an embodiment of the invention that can be used for monitoring the ingestion of food and/or drink by the subject. The apparatus 2 comprises a control unit 4 that controls the operation of the apparatus 2 and that can implement the monitoring method. Briefly, the control unit 4 is configured to process measurements of a physiological characteristic for a subject to determine a frequency for the physiological characteristic, set a cut-off frequency for a filtering stage, filter eddy current measurements using the filtering stage to remove signal components due to the physiological characteristic, and then determine whether food and/or drink is present in the stomach based on the filtered signal. The control unit 4 can comprise one or more processors, processing units, multi-core processors or modules that are configured or programmed to control the apparatus 2 to monitor the subject as described below.

In particular implementations, the control unit 4 can comprise a plurality of software and/or hardware modules that are each configured to perform, or are for performing, individual steps in the monitoring method according to embodiments of the invention. As such, the control unit 4 (or more generally the apparatus 20) can comprise a First Obtaining module 6, Second Obtaining module 8, Setting module 12, Filtering module 12 and Processing module 14, that can each implement the functions required for performing steps 101-109 of FIG. 4 respectively, and which are described in more detail below.

The apparatus 2 can also comprise a memory unit 18 that can be used for storing program code that can be executed by the control unit 4 to perform the method described herein. The memory unit 18 can also be used to store signals and measurements made or obtained by any sensors in the apparatus (including a measurement coil 22 or other component for measuring an eddy current, and a physiological characteristic sensor 24).

In some embodiments, the apparatus 2 can comprise an excitation coil 20 (or other component for creating a magnetic field) for generating (inducing) an eddy current in the subject under the control of the control unit 4, a measurement coil 22 (or other component for measuring an eddy current in the subject) and/or one or more physiological characteristic sensors 24 for measuring one or more physiological characteristics of the subject. The measurements of the eddy current and physiological characteristic(s) can be processed as the measurements are obtained (e.g. in real-time), or they can be stored in the memory unit 18 and the control unit 4 can retrieve and process the previously-obtained measurements from the memory unit 18 at a later time.

In alternative embodiments, the excitation coil 20, measurement coil 22 and/or physiological characteristic sensor(s) 24 (with appropriate control circuitry for those components) can be separate from the apparatus 2, and the measurements of the eddy current and/or measurements of the physiological characteristic(s) can be provided to the apparatus 2, for example via a wired or wireless connection, for subsequent analysis.

In some embodiments the control unit 4 (and thus the apparatus 2) may be part of a smart phone or other general purpose computing device that can comprise, be connected to or otherwise receive a measurement signal from a physiological characteristic sensor 24 and a measurement coil 22, but in other embodiments the apparatus 20 can be an apparatus that is dedicated to the purpose of monitoring a subject to determine the presence of food and/or drink in the stomach of the subject. In embodiments where the control unit 4 is part of a smart phone or other general purpose computing device, then depending on the physiological characteristic to be monitored, the sensor 16 could be a sensor that is integrated into the smart phone, or a sensor that is separate to the smart phone and that can provide sensor signals/measurements to the smart phone/computing device for processing and analysis (for example via a wired or wireless connection).

The physiological characteristic sensor 24 measures one or more physiological characteristics of a subject. In some embodiments the physiological characteristic is heart rate, and thus the physiological characteristic sensor 24 can be any sensor that is capable of or suitable for measuring heart rate. Thus, the physiological characteristic sensor 24 can be a heart rate sensor, such as an accelerometer, an electrocardiogram (ECG) (which includes, for example, a plurality of electrodes), a photoplethysmogram (PPG), a microphone, etc. In some embodiments the physiological characteristic is breathing rate (also referred to as respiration rate), and thus the physiological characteristic sensor 24 can be any sensor that is capable of or suitable for measuring the breathing rate. Thus, the physiological characteristic sensor 24 can be a breathing rate sensor, such as an accelerometer, an electrocardiogram (ECG), a strain gauge (for measuring the change in the circumference of the chest as the subject breathes), a microphone, etc. The output of the physiological characteristic sensor 24 may be a time series of values for the physiological characteristic, or 'raw' measurements (e.g. acceleration measurements) that are processed by the control unit 4 in order to determine a time series of values for the physiological characteristic.

It will be appreciated that in some embodiments multiple physiological characteristics can be measured, and it is possible for a single physiological characteristic sensor 24 to be used to measure those physiological characteristics. For example the measurement signal from an accelerometer that is worn on the upper body of the subject can be processed to determine the heart rate and the breathing rate. Alternatively the signals in an ECG can be analysed to determine the heart rate and the breathing rate.

In some embodiments, the apparatus 2 can further comprise a temperature sensor that is to be worn on the subject's body near the stomach in order to measure changes in temperature related to digestion.

It will be appreciated that FIG. 1 only shows the components required to illustrate this aspect of the invention, and in a practical implementation the apparatus 2 will comprise additional components to those shown. For example, the apparatus 2 may comprise a battery or other power supply for powering the apparatus 2 or means for connecting the apparatus 2 to a mains power supply, and/or a communication module for enabling the measurements of the physiological characteristic and/or measurements of the eddy current of the subject to be communicated to a base unit for the apparatus 2 or a remote computer. The apparatus 2 may also comprise at least one user interface component that is for use in providing the subject or other user of the apparatus 2 (for example a family member or healthcare provider) with information resulting from the method according to the invention. For example the user interface component can provide an indication of whether food and/or drink is present in the stomach of the subject, or was present in the stomach at a selected time. Alternatively or in addition the user interface component can provide an indication of when food and/or drink was present in the stomach over a time interval. The user interface component can comprise any component that is suitable for providing the above information, and can be, for example, any one or more of a display screen or other visual indicator, a speaker, one or more lights, and a component for providing tactile feedback (e.g. a vibration function).

In addition, the user interface component is or comprises some means that enables the subject or another user of the apparatus 2 to interact with and/or control the apparatus 2. For example, the user interface component could comprise a switch, a button or other control means for activating and deactivating the apparatus 2 and/or the monitoring process.

Figure 2:
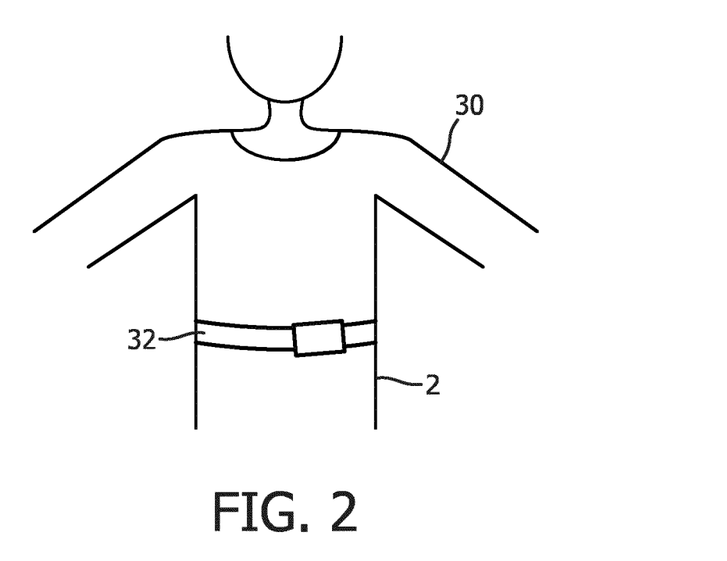
FIG. 2 shows an apparatus according to an embodiment of the invention being worn by a subject.
Figure 3:
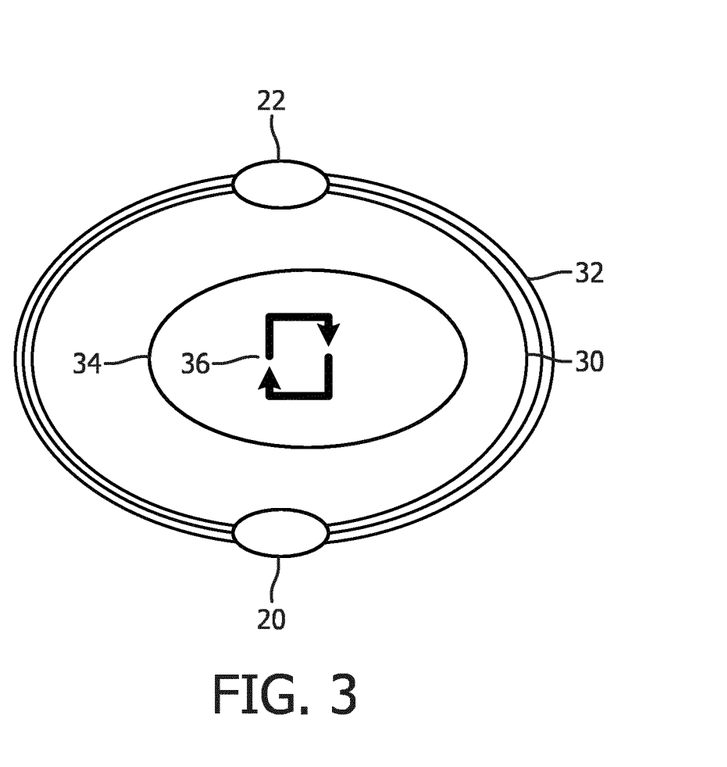
FIG. 3 shows a cross-section through a subject and the apparatus.

FIG. 2 shows an apparatus 2 according to the invention being worn by a subject 30. In this embodiment the apparatus 2 comprises a strap 32 or other form of attachment means that enables the apparatus 2 to be held in place around the body of the subject so that the excitation coil 20 applies a magnetic field to the part of the body comprising the stomach, and the measurement coil 22 measures the eddy current generated in that part of the body. It is not necessary for the apparatus 2 to be worn against the FIG. 3 shows a cross-section through a subject 30 that is wearing an apparatus 2 according to the invention that uses a strap 32 to hold the apparatus 2 on the subject 30. A cross-section through the stomach 34 is shown, along with an eddy current 36 that is induced by a magnetic field generated by excitation coil 20, and that is measured by measurement coil 22. It will be appreciated that although the excitation coil 20 and the measurement coil 22 are shown as being generally located on opposite sides of the body of the subject 30, the coils 20, 22 can be located on the same side of the subject 30, although care will need to be taken with their positioning in order to avoid the effects of cross-talk from the excitation coil 20 on the measurement coil 22.

Figure 4:
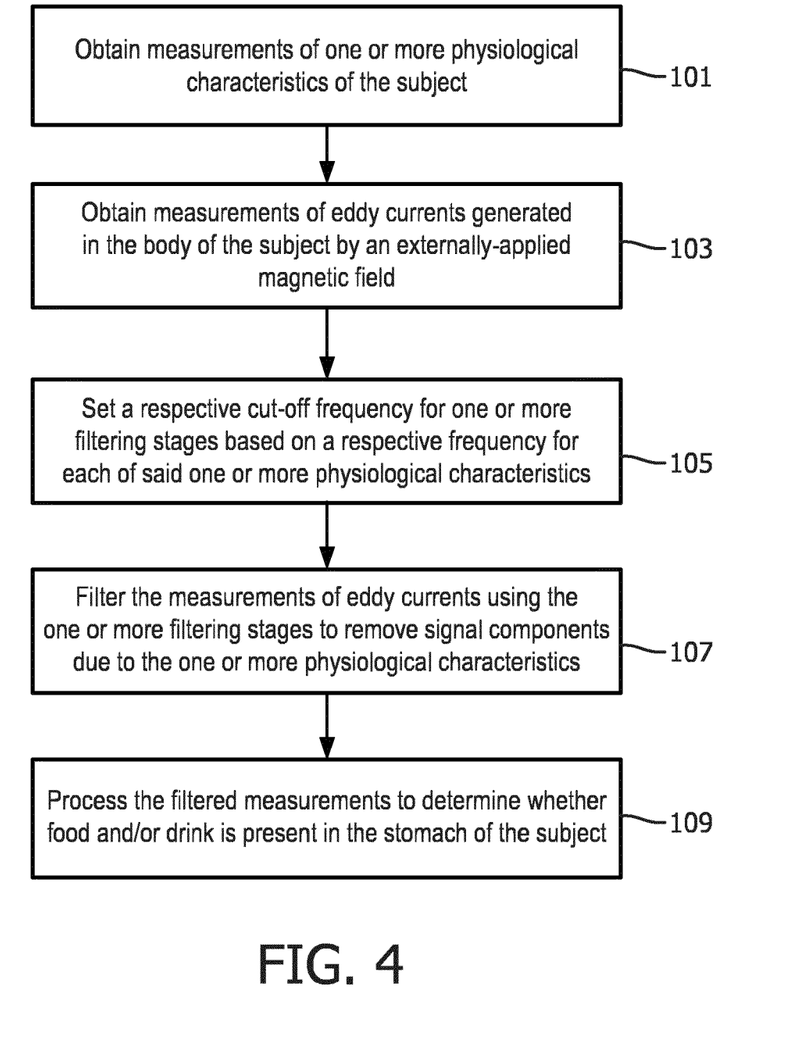
FIG. 4 is a flow chart illustrating a method according to an embodiment of the invention.
Figure 5A:
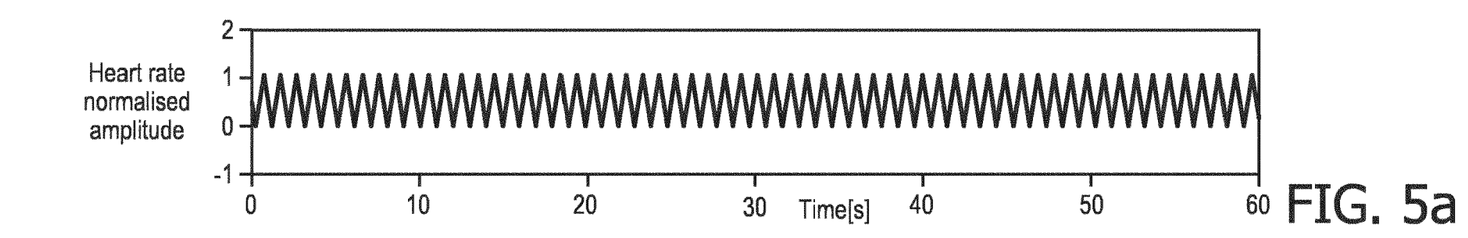
FIG. 5 shows different physiological characteristic measurements and a peristaltic component and a food intake signal determined according to embodiments of the invention.
Figure 5B:
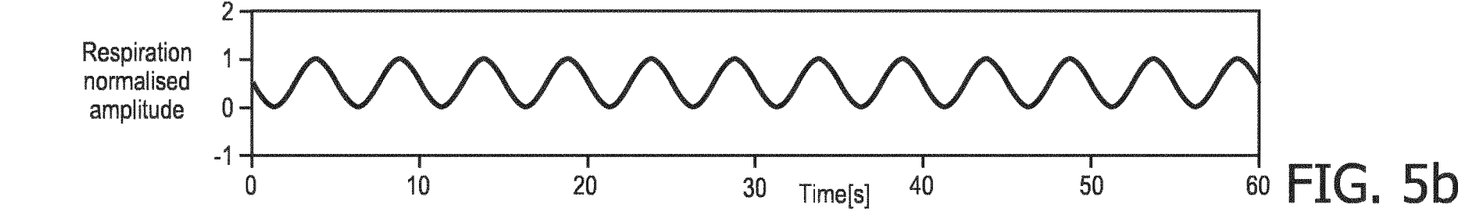
Figure 5C:
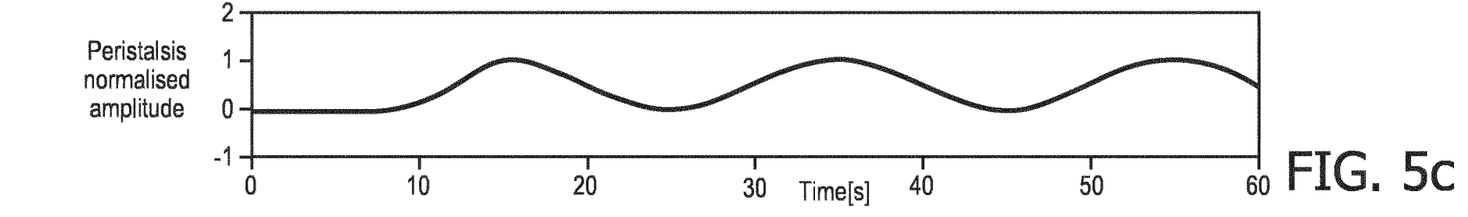
Figure 5D:
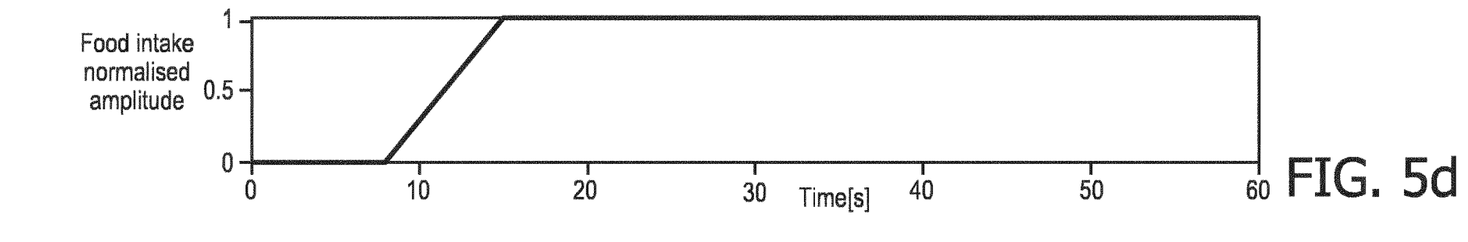

FIG. 4 illustrates a method of monitoring the ingestion of food and/or drink by a subject 30 according to the invention. This method can generally be performed by or under the control of control unit 4.

In a first step, step 101, which can be performed or implemented by the first obtaining module 6, measurements of one or more physiological characteristics of the subject 30 are obtained. These measurements can be obtained directly from a physiological characteristic sensor 24, or retrieved from memory unit 18. The measurements typically cover a period of time, e.g. a few seconds, minutes, etc. As noted above, the output of the physiological characteristic sensor 24 may be a time series of values for the physiological characteristic, or 'raw' measurements (e.g. acceleration measurements). In the latter case, step 101 may comprise processing the raw measurements to determine measurements of the physiological characteristic. In preferred embodiments the physiological characteristic(s) can be heart rate and/or breathing rate, and thus the measurement(s) of the physiological characteristic(s) can be represented as a frequency (e.g. beats per minute, breaths per minute, etc.).

In a second step, step 103, which can be performed or implemented by the second obtaining module 8, measurements of eddy currents generated in the body of the subject 30 by an externally-applied magnetic field are obtained. These measurements can be obtained directly from a measurement coil 22, or retrieved from memory unit 18. The measurements of eddy currents may cover a substantial amount of time, e.g. a few hours, days, etc. Where the measurements are obtained directly from a measurement coil 22, the method may also comprise generating a magnetic field in the subject 30 using the excitation coil 20 (for example by supplying a current to the excitation coil 20).

Preferably the measurements of the one or more physiological characteristics of the subject 30 are made at the same or at a similar time to the measurements of the eddy currents.

Next, in step 105, which can be performed or implemented by the setting module 10, for each measured physiological characteristic, a cut-off frequency in a filtering stage is set based on the measurements of that physiological characteristic. Since the peristalsis component and the signal component that increases and decreases with the content of the stomach are signals having a lower frequency than the physiological characteristic (e.g. heart rate and/or breathing rate), the filtering stage preferably performs low-pass filtering of an input signal to pass frequency components below the cut-off frequency and thereby remove signal components having a frequency above the cut-off frequency. In some embodiments the cut-off frequency can be set at the value of the physiological characteristic (e.g. the cut-off frequency is set at the measured heart rate or breathing rate). However, since the value of the physiological characteristic is measured (estimated) from a sensor signal and the value of the physiological characteristic can vary slowly over time, it is preferable for the cut-off frequency to be set to a value that ensures that the contribution of the physiological characteristic to the eddy current measurements is filtered out. Thus, in some embodiments the cut-off frequency can be set to the value of the physiological characteristic less some (small) predetermined offset. For example the offset can be 0.05 Hz or 0.1 Hz).

In some embodiments there can be respective filtering stages for each of the measured physiological characteristics, with the cut-off frequency for each filtering stage being set based on the measurements for a respective one of the physiological characteristics. Preferably however there is a single filtering stage, and the cut-off frequency for that filtering stage is set based on the lower of the frequencies associated with the measured physiological characteristics. For example if heart rate and breathing rate are measured, the lower of the two physiological characteristics is used to set the cut-off frequency for the low-pass filtering stage.

In some embodiments, instead of using a low-pass filter, it is possible to use a band-stop filter, with the stop band or stop bands (if multiple physiological characteristics are measured) being based on the measured value of the physiological characteristic(s).

Once the cut-off frequency(ies) has/have been set in step 105, the eddy current measurements are filtered using the filtering stage(s) in step 107 in order to remove signal components due to the one or more physiological characteristics. Step 107 can be performed or implemented by filtering module 12.

The filtered measurements are then processed to determine whether food and/or drink is present in the stomach of the subject (step 109). Step 109 can be performed or implemented by processing module 14.

In a simple embodiment, step 109 can comprise determining the amplitude of the filtered signal at a particular time instant and comparing the amplitude to a threshold. For example it can be determined that there is food and/or drink present in the stomach of the subject at a particular time instant if the amplitude of the signal at that time instant is above the threshold.

In a more preferred embodiment, which reduces the effects of drift in the measurements of the eddy currents, step 109 comprises determining an amount by which the amplitude of the filtered signal has changed over a predetermined time window (e.g. with a duration of a few seconds, a minute, etc.) and comparing the change to a threshold. Those skilled in the art will be aware of ways in which this amount can be determined, and for example the amount can be determined as the difference between the maximum and minimum amplitudes in the time window, or the amount can be determined as the difference between the amplitude at the start of the window and the amplitude at the end of the time window. If the amplitude has increased by more than the threshold amount during the time window, it can be determined that food and/or drink is now present in the stomach. If the amplitude has decreased by more than the threshold amount during the time window, it can be determined that food and/or drink is no longer present in the stomach.

In other embodiments, step 109 can comprise using machine learning techniques to analyse the filtered eddy current signal to determine when food and/or drink has entered and/or left the stomach. With these types of techniques, the presence of food and/or drink in the stomach can be inferred from the filtered (time-dependent) eddy current signal or from features extracted from the filtered (time-dependent) eddy current signal.

In some embodiments, step 109 can comprise processing the filtered measurements to identify a signal relating to peristalsis. For example, a frequency decomposition of the filtered eddy current measurements can be performed to separate the generally periodic signal due to peristalsis from the constant (DC) component due to the content/composition of the body and the component that increases and decreases with the content of the stomach. After separation of the signal due to peristalsis, the remaining eddy current signal components can be compared with the preceding parts of the signal to identify whether an increment due to food and/or drink ingestion has occurred (e.g. in a similar way to the more preferred embodiment above). Alternatively, as noted above, in some embodiments, after the separation of the signal due to peristalsis, the amplitudes of the remaining eddy current signal components can be compared to a threshold to identify whether food and/or drink is present in the stomach of the subject.

It will be appreciated that in the above embodiments the peristalsis component is effectively removed from the eddy current measurements and the remaining measurements are processed to determine if there is an increase consistent with food and/or drink entering the stomach. However, in preferred embodiments, the determination that food and/or drink is present in the stomach can be conditional on detecting both a generally periodic signal due to peristalsis (i.e. peristalsis is occurring) and an increase in the remaining eddy current signal components over a time window (or the amplitude of the eddy current signal being above a threshold).

FIG. 5 illustrates signals representing exemplary physiological characteristics and whether food and/or drink is present in the stomach following the processing according to the invention. In each of FIGS. 5(*a*)-(*d*), the x-axis represents time in seconds, and the y-axis represents the normalized amplitude of the relevant signal. Thus, FIG. 5(*a*) is a heart rate signal with a frequency of 1 Hz (i.e. 60 beats per minute), and FIG. 5(*b*) is a respiration rate signal with a frequency of 0.2 Hz (i.e. 12 breaths per minute). As described above the frequencies associated with the physiological characteristic in FIGS. 5(*a*) and (*b*) are used by a filtering stage (or respective filtering stages) to remove eddy current components due to those characteristics. FIG. 5(*c*) shows a peristalsis signal derived from a filtered eddy current signal that shows that peristalsis starts at around 8 seconds and continues for the rest of the measurement period with a frequency of around 0.05 Hz (i.e. around 3 contractions per minute). FIG. 5(*d*) shows a food intake signal obtained from the remaining eddy current measurements after separation of the peristalsis components where a value of 0 represents no food in the stomach and a value of 1 represents food being present in the stomach. Thus it can be seen that in this example between 8 and 15 seconds there is an increase in the signal due to food reaching the stomach.

It will be appreciated that the method in FIG. 4 can be performed frequently, semi-continuously or continuously, in which case it may be possible to detect the times at which food and/or drink is ingested, the duration for which food and/or drink is ingested, and/or the times at which the stomach is empty.

In some embodiments, as described in more detail below, the filtered measurements can be processed to identify if the conductivity of the stomach has increased (which indicates the ingestion of food and/or drink) or decreased (which indicates that chyme has passed into the intestines). In some cases the filtered measurements can be processed into conductivity measurements, but in other cases the analysis can operate directly on the filtered current measurements. In some embodiments, the amount of food and/or drink ingested can be estimated based on the magnitude of the change in conductivity.

The eddy current density $\vec{J}$ in living tissue is governed by the following diffusion equation:

$$\nabla^2 \vec{J} = \sigma \mu \frac{\partial \vec{J}}{\partial t} \qquad [1]$$

where $\sigma$ is the electrical conductivity, and $\mu$ is the permeability of a living tissue specimen. Considering this equation it can be seen that a change in the electric and magnetic proprieties of the living tissue changes the eddy current density. Therefore, analysis of the measurements of the eddy current gives information about the status of the living tissue.

As noted above, the biological medium in the region of the stomach changes principally because of (i) heart rate (the contraction and relaxation of blood vessels due to heart beats); (ii) respiration (the movement of the diaphragm muscle and movement of the thoracic cavity); (iii) peristalsis (the contraction and relaxation of the muscles of the digestive tract that propels the chyme out of the stomach); and (iv) the introduction of food and/or drink (the medium will present the combination of the electric and magnetic proprieties of biological tissue and the chyme present in the stomach). Where food and/or drink has not been ingested (and any previously-ingested food and/or drink has been moved out of the stomach), elements (iii) and (iv) will not be present or will not affect the eddy current.

As previously described, the effects of (i), (ii) and (iii) above on the eddy current are easily understandable (due to changes in the volume of the medium in which the current is generated), but (iv) influences the eddy currents through a combination of geometrical and electrochemical changes. The geometrical change is due to the presence of the food and/or drink in the stomach, and the electrochemical change is due to the digestion process. During this biological process the stomach releases a high quantity of acid (with high $H^+$ concentration) that influences the conductivity of the medium as follows:

$$\sigma(\omega) = \sigma_I + \omega \varepsilon_0 \varepsilon'' \quad [2]$$

$$\sigma_I = q \Sigma z_i n_i u_i \quad [3]$$

Where $\sigma_I$ is the conductivity arising from the electric-field induced motions of the various ions in the electrolyte. In the case of the stomach during digestion, it is possible to consider predominant $H^+$ as an ionic species so z, n and u are the valency, the concentration and the electrical mobility of the $H^+$ respectively. When no food and/or drink is ingested, the $H^+$ concentration due to digestion is near to 0 mole, so there is no change in the conductivity of the stomach.

The result of the processing in step 109 can be presented to the subject or another user of the apparatus 2 (for example a healthcare provider) using a user interface component in the apparatus 2. The result can be presented in any suitable or desired form. For example the result can be presented as an indication of whether food and/or drink is present in the stomach or an indication of whether food and/or drink has been ingested by the subject. The indication can be provided in a simple form, such as a light or other visual indicator, or it can be presented as a written or spoken message, or presented in a graphical format, perhaps illustrating the times at which food has been ingested/food was present in the stomach.

In some embodiments, the measurements of the physiological characteristics (or the measurements from the physiological characteristic sensor 24) can be used to determine whether it will be useful to measure and/or analyse eddy currents at that time. For example if the subject is exercising or otherwise quite physically active, they are unlikely to eat during that time, so the measurements of the physiological characteristics can be analysed to determine if the subject is active (e.g. the subject can be deemed to be active if the heart rate is above a heart rate threshold and/or the breathing rate is above a breathing rate threshold), and if so the control unit 4 will stop generating a magnetic field using the excitation coil 20 and/or stop the processing of that segment of the measurements of the eddy currents associated with the high activity. If it is determined that the subject is less physically active (e.g. the heart rate is below the heart rate threshold and/or the breathing rate is below the breathing rate threshold), then the control unit 4 can control the excitation coil 20 to generate a magnetic field and measure the eddy currents using the measurement coil 22 and/or start/continue the processing of that segment of the measurements of the eddy currents associated with the low activity level. In addition or alternatively, a measure of the level of physical activity of the subject can be obtained using an accelerometer (which may be the same accelerometer as used to measure the physiological characteristic, or a separate or additional accelerometer). In that case the level of physical activity (which can, for example, be obtained by analysing the magnitude of the accelerometer measurements) can be compared to a threshold, and if the level of physical activity is above the threshold, the control unit 4 can stop generating a magnetic field using the excitation coil 20 and/or stop the processing of that segment of the measurements of the eddy currents associated with the high activity level.

In addition or alternatively, since the temperature of the stomach tends to increase when food and/or drink is present (due to the digestion process), the temperature of the stomach region can be measured by a temperature sensor and the generation of a magnetic field and measurement of eddy currents triggered when the temperature is above a temperature threshold (e.g. above 40° C.).

In embodiments where the eddy current measurements are analysed over a time window to determine a change that may be due to food and/or drink entering the stomach, it may be desirable to check whether the subject is in the same posture throughout the time window. In particular, this is useful as the eddy current measurements can be affected by a change in the posture of the subject. The posture can, for example, be determined using an accelerometer (whether the same accelerometer used to measure the physiological characteristic(s), or a separate accelerometer included in the apparatus 2), by analysing the orientation (direction) of the gravity acceleration vector with respect to the axis of the accelerometer. Alternatively a gyroscope or another type of sensor could be used to determine the posture.

Figure 6:
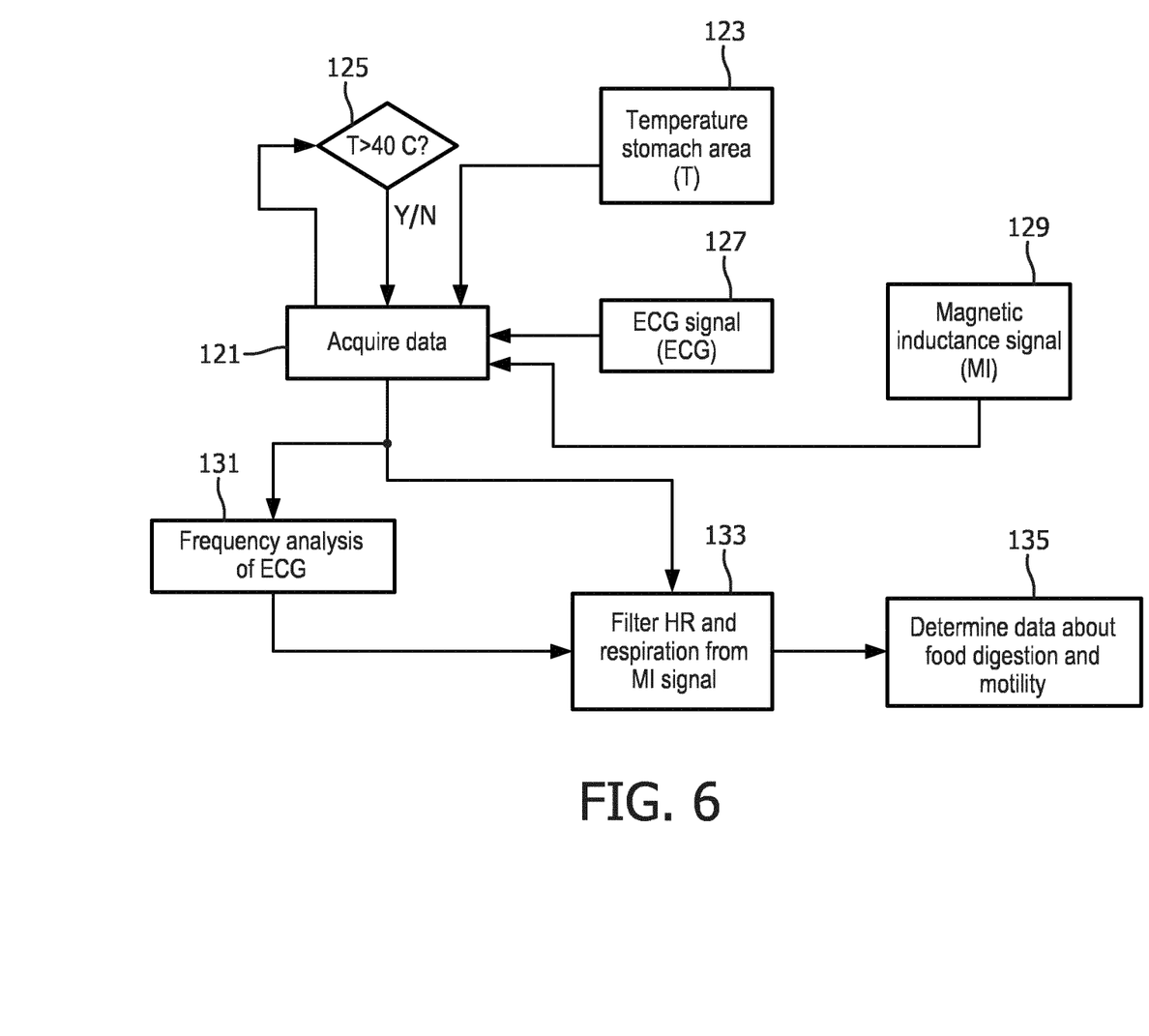
FIG. 6 is a flow chart illustrating a method according to an embodiment of the invention.

The diagram in FIG. 6 illustrates a specific method according to an embodiment of the invention. In this embodiment an ECG is used to measurement the heart rate and respiration rate, and a temperature sensor is used to trigger the start of the monitoring process.

Thus, at block 121 data/measurements are acquired from a temperature sensor that measures the temperature (T) in the stomach region (block 123). This temperature T is compared to a threshold temperature that is used to determine whether digestion is taking place in the stomach (block 125). The threshold can be 40° C., although other values can be used. If T is below the threshold, then the temperature is monitored until it exceeds the threshold. Once T exceeds the threshold, block 121 collects ECG measurements/data from an ECG sensor (block 127) and measurements of eddy currents (shown as a magnetic inductance (MI) signal)—block 129.

A frequency analysis of the ECG signal is then performed in order to determine the heart rate and breathing rate (block 131) and these rates (frequencies) are used to filter heart rate and respiration rate components from the MI signal (block 133), as in step 107 above. The filtered signal is then analysed to determine information about the presence of food, food digestion and motility (block 135). Optionally this information can then be displayed to the subject or another user of the apparatus 2.

There is therefore provided an improved method and apparatus that provides a non-invasive and generally unobtrusive solution for monitoring the ingestion of food and/or drink by a subject.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An apparatus for monitoring the ingestion of food and/or drink by a subject, the apparatus comprising:
 a control unit that comprises:
  a first obtaining module configured to obtain measurements of one or more physiological characteristics of the subject;
  a second obtaining module configured to obtain measurements of eddy currents generated in the body of the subject by an externally-applied magnetic field;
  a setting module configured to set a respective cut-off frequency for one or more filtering stages based on a respective frequency for each of said one or more physiological characteristics;
  a filtering module configured to filter the measurements of eddy currents using the one or more filtering stages to remove signal components due to the one or more physiological characteristics; and
  a processing module configured to process the filtered measurements to determine whether food and/or drink is present in the stomach of the subject.

2. An apparatus as claimed in claim 1, wherein the one or more physiological characteristics comprises one or more of heart rate and breathing rate.

3. An apparatus as claimed in claim 1, wherein the processing module is configured to process the filtered measurements to determine whether food and/or drink is present in the stomach of the subject by:
 comparing the amplitude of the filtered measurements at a time instant to a threshold.

4. An apparatus as claimed in claim 3, wherein the processing module is further configured to process the filtered measurements to determine whether food and/or drink is present in the stomach of the subject by:
 determining that food and/or drink is present in the stomach if the amplitude at the time instant is above the threshold.

5. An apparatus as claimed in claim 3, wherein the processing module is further configured to process the filtered measurements to determine whether food and/or drink is present in the stomach of the subject by:
 processing the filtered measurements to identify a signal relating to peristalsis in the subject; and
 determining that food and/or drink is present in the stomach of the subject if the amplitude at the time instant is above the threshold and the signal relating to peristalsis indicates that peristalsis is occurring in the subject.

6. An apparatus as claimed in claim 1, wherein the processing module is configured to process the filtered measurements to determine whether food and/or drink is present in the stomach of the subject by:
 determining an amount by which the amplitude of the filtered measurements has changed over a predetermined time window; and
 comparing the amount by which the amplitude of the filtered measurements has changed over the predetermined time window to a threshold.

7. An apparatus as claimed in claim 6, wherein the processing module is further configured to process the filtered measurements to determine whether food and/or drink is present in the stomach of the subject by:
 determining that food and/or drink is present in the stomach if the amount is above the threshold.

8. An apparatus as claimed in claim 6, wherein the processing module is further configured to process the filtered measurements to determine whether food and/or drink is present in the stomach of the subject by:
 processing the filtered measurements to identify a signal relating to peristalsis in the subject; and
 determining that food and/or drink is present in the stomach of the subject if the amount is above the threshold and the signal relating to peristalsis indicates that peristalsis is occurring in the subject.

9. An apparatus as claimed in claim 1, wherein the apparatus further comprises:
 an excitation coil for generating an eddy current in the subject; and
 a measurement coil for measuring the eddy current in the subject.

10. An apparatus as claimed in claim 1, wherein the apparatus further comprises:
 one or more physiological characteristic sensors for obtaining the measurements of the one or more physiological characteristics of the subject.

* * * * *